(12) United States Patent
Bandyopadhyay et al.

(10) Patent No.: US 6,773,728 B2
(45) Date of Patent: Aug. 10, 2004

(54) **HERBAL COMPOSITION OF BLEND OF ACTIVE COMPONENTS PREPARED FROM *MURRYA KOENIGII* AND *PIPER BETLE* USEFUL FOR BLOCKING OF 5 LIPOXYGENASE ACTIVITY LEADING TO THE INHIBITION OF LEUKOTRIENE SYNTHESIS, SUPPRESSION OF INTERLEUKIN-4 PRODUCTION, AND ENHANCEMENT OF GAMMA INTERFERON RELEASE**

(75) Inventors: Santu Bandyopadhyay, Kolkata (IN); Keshab Chandra Roy, Kolkata (IN); Mitali Roy, Kolkata (IN); Bikash Chandra Pal, Kolkata (IN); Ranjan Bhadra, Kolkata (IN); Krishna Das, Kolkata (IN); Samir Bhattacharya, Kolkata (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/985,160

(22) Filed: Nov. 1, 2001

(65) Prior Publication Data

US 2002/0086068 A1 Jul. 4, 2002

Related U.S. Application Data

(63) Continuation-in-part of application No. 09/925,415, filed on Aug. 10, 2001, which is a continuation of application No. PCT/IN00/00102, filed on Oct. 16, 2000.

(30) Foreign Application Priority Data

Oct. 18, 2000 (WO) .................. PCT/IN00/00127

(51) Int. Cl.$^7$ .................................... A61K 35/78
(52) U.S. Cl. ............................................ 424/725
(58) Field of Search ............................ 424/725

(56) References Cited

FOREIGN PATENT DOCUMENTS

| GB | 1445599 | * | 8/1976 |
| JP | 08283171 | * | 10/1996 |
| JP | 409278666 | * | 10/1997 |

OTHER PUBLICATIONS

Vaijayanthimala et al., Phytotherapy Research, 14(3), 207–209, May 2000.*

* cited by examiner

*Primary Examiner*—Michael Meller
(74) *Attorney, Agent, or Firm*—Foley & Lardner LLP

(57) ABSTRACT

This invention relates to an herbal composition for the treatment and remedy of bronchial respiratory difficulties, more particularly this invention describes the process of separation, physicochemical characterization and biological response evaluation of active components obtained from extracts of any plant parts including leaves, barks, roots and seeds of plants *M. koenigii* and *P. betle* in order to establish their role on the treatment and remedy of bronchial respiratory troubles.

18 Claims, 2 Drawing Sheets

HERBAL COMPOSITION OF BLEND OF ACTIVE COMPONENTS PREPARED FROM *MURRYA KOENIGII* AND *PIPER BETLE* USEFUL FOR BLOCKING OF 5 LIPOXYGENASE ACTIVITY LEADING TO THE INHIBITION OF LEUKOTRIENE SYNTHESIS, SUPPRESSION OF INTERLEUKIN-4 PRODUCTION, AND ENHANCEMENT OF GAMMA INTERFERON RELEASE

CROSS-REFERENCE TO RELATED PATENT APPLICATIONS

This application is continuation in part of Ser. No. 09/925,415 filed Aug. 10, 2001, which is a continuation of PCT/IN00/00102, filed Oct. 16, 2000, incorporated herein by reference in its entirety, and PCT/IN00/00127, filed Dec. 18, 2000, incorporated herein by reference in its entirety.

BACKGROUND OF THE INVENTION

1. Field of the Invention

This invention relates to an herbal composition for the treatment and remedy of bronchial respiratory difficulties. More particularly this invention describes the process of separation, physicochemical characterization and biological response evaluation of active components obtained from extracts of any plant parts including leaves, barks, roots and seeds of plants *M. koenigii* and *P. betle* in order to establish their role on the treatment and remedy of bronchial respiratory troubles.

2. Background and Prior Art References

Respiratory problem consists of mild to extremely severe trouble of breathing along with the other discomforts such as wheezing, coughing, chest tightness and the like. In spite of precautionary measure, public awareness campaign and monitoring system, population having respiratory trouble is on the rise all over the world. This is true in western advanced countries, especially among the children. Using *M. koenigii* leaf preparation, the relief and possible cure of asthma has already been demonstrated by the applicants in their PCT Patent application No: PCT/IN/00102 filed on dated Oct. 16, 2000. Two-prong strategy is adapted in the present invention.

The respiratory disease is the result of pathophysiological symptoms arising out of aberration of immune system. The immediate symptom includes bronchial constriction, inflammation of respiratory tract and closing of air way by mucus secretion. The symptomatic drugs provide relief by temporary relaxation of the distressed symptoms.

The root cause for respiratory problems is not well addressed by the developers of symptomatic drugs. With the advent of current knowledge, it is now well accepted that leukotrienes are found to be the main player in developing symptoms of respiratory problems.

The major symptoms of respiratory problem can be divided into early and late responses. The early response occurs within minutes of allergen exposure and involves primarily mediators such as histamine, leukotrienes and prostaglandin D2. The effects of these mediators result in bronchocontriction and accumulation of mucus. The late response occurs hours later and involves additional mediators including IL-4, IL-5, IL-6, and TNF-alpha, eosinophils chemotactic factor (ECF) and platelet aggregation factor (PAF). The overall effect of these mediators is to recruit inflammatory cells including eosinophils and neutrophils. These cells are capable of causing significant tissue injury by releasing toxic enzymes. These events lead to occlusion of bronchial lumen with mucus protein, and cellular debris, thus thickening of basement membrane, fluid build up and hypertrophy of the bronchial smooth muscle. A mucus plug often forms and adheres to the bronchial wall. The mucus plug contains clusters of detached epithelial cells fragments, eosinophils, some neutrophils and spirals of bronchial tissue known as Curschmann's spiral (Immunology, J. Kuby; W. H. Freeman & Co., New York; 3rd edition 1997). In view of the current mechanisms regarding manifestation of bronchial asthma/bronchial respiratory problems, modern strategy for drug development stressed the following approaches:

These include i) inhibition of leukotriene synthesis via blocking the 5-lipoxygenase-enzyme activity (Leqqis R A et al New England J. Med. 323:, 645,1990). The formation of leukotrienes originates from the oxidation of arachidonic acid, hence inhibition of this reaction leads to the inhibition of leukotriene synthesis. Besides, leukotriene receptors antagonists have also been introduced as anti leukotriene therapy for asthma/respiratory problems (Tien F. C., Medical J. Aust. 171: 378,1999). Currently licensed drug zelutin, based on inhibition of arachidonic acid oxidation has already been introduced exclusively in the US market. However, its use is limited by hepatotoxicity. Children below 14 years are not recommended for this drug. Moreover, patients taking other drugs need to be surveyed when taking zelutin as anti-asthma drug. More over patients taking other drugs, need to be surveyed when taking zelutin, as anti-asthma drug. ii) the neutralization of IgE either by anti-IgE antibody (humanized) or by blocking the high affinity IgE receptor, FcεR-I (Heusser C, Jardiu P. Current Oppinio Immunol., 9: 805,1999). Since suppression of Th2 cytokines leads to decrease in IgE production, additional approach is based on the inhibition of these Th2 cytokine synthesis and enhancement of Th1 cytokine formation (Chung K. F.; Barens P. J. Thorax 54: 825, 1999).

In contrast, *M. koenigii* based anti asthmatic preparation has been tried on children as young as 7 years old and octogenarian as old as 80 years and above without any adverse reaction.

The fractions of *M. koenigii* extracts obtained from all plant parts including leaves, barks, roots and seeds are therefore examined to identify the active components. These are based on their potential to inhibit the production of leukotrienes. Additionally, the fractions are also examined for shifting of Th2 response towards to Th1 type. Th1 and Th2 response are measured by γ-interferon (Th1) and IL-4 (Th2) production respectively. Some *M. koenigii* fractions showed inhibition of 5-lipoxygenase mediated arachidonic acid oxidation signifying blockage of leukotriene synthesis and remarkable increase in γ-interferon production which in turn would suppress IL-4 production. On the other hand, most of the *P. betle* leaf extract-fractions resulted in facilitating of the shift from Th2 type response to Th1 type. Thus, a blend of selected extract components from these two plants *M. koenigii* and *P. betle* predominantly inhibited leukotriene synthesis and shifted Th2 response towards Th1 type and therefore is proposed as a unique synergistic composition for treatment, relief and remedy of bronchial respiratory problems Thus the two pronged strategy is the major objective of this new composition and can be considered as the best modality of treatment for patients bronchial respiratory problems.

OBJECTS OF THE INVENTION

The main object of the invention is to provide the bioactive fractions, which are obtained from the plants parts of *Murraya koenigii* and *Piper betle*.

Another object of the invention is to provide a new composition comprising combination of active components derived from *Murraya koenigii* and *Piper betle* plant parts for treating respiratory problems.

Another object of the present invention is to provide a process for the isolation of active components from the plant parts of *M. koenigii* and *P. betle* useful for relief, treatments and remedy of respiratory problems.

Yet another objective of the present invention is to provide a simplified method of isolation of active components from all plant parts of *M. koenigii* and *P. betle* possessing biological activities relevant to treatment, relief and remedy of respiratory problems.

Yet another objective of the present invention is to provide a simplified fast and inexpensive process for the preparation of a composition possessing biological activities relevant to treatments, relief and remedy of respiratory problems.

Yet another objective of the present invention is to provide a herbal composition preparation, comprising of active factors and components derived from all plant parts of *M. koenigii* and *P. betle*, wherein the said factors and components being highly compatible for human consumption and the treatments, relief and remedy of respiratory problems.

Yet another objective of the present invention is to examine each of the active components individually or in combination from all plant parts *M. koenigii* and *P. betle* leaves having inhibitory activity of 5-lipoxygenase mediated Arachidonic acid oxidation and promoting the shift of Th2 type response towards Th1 type.

Yet another objective of the present invention is to assay 5-lipoxygenase mediated Arachidonic acid oxidation in an ex vivo whole human blood system in the presence of *M. koenigii* and *P. betle* components individually and in combination.

Yet another objective of the present invention is to assay the 5-lipoxygenase mediated Arachidonic acid oxidation in ex vivo systems with enriched human polymorphonuclear neutrophils (PMN) in the presence of *M. koenigii* and *P. betle* components individually and in combination.

Yet another objective of the present invention is to detect the production of intracellular cytokines by flowcytometry.

Yet another objective of the present invention is to provide intracellular IFN-gama and IL-4 profile as known markers for Th1 and Th2 type response respectively in ex vivo human whole blood with the components from all plant parts of *M. koenigii* and *P. betle* individually and in combination.

SUMMARY OF THE INVENTION

Accordingly, the present invention provides an herbal composition useful for the treatment and remedy of bronchial respiratory difficulties. Another aspect of the invention, particularly describes a process of separation, physico-chemical characterization and biological response evaluation of active components obtained from the extracts of any plant parts including leaves, barks, roots and seeds of plants *M. koenigii* and *P. betle* in order to establish their role on the treatment and remedy of bronchial respiratory troubles.

DETAILED DESCRIPTION OF THE PREFERRED EMBODIMENTS

Figure 1:
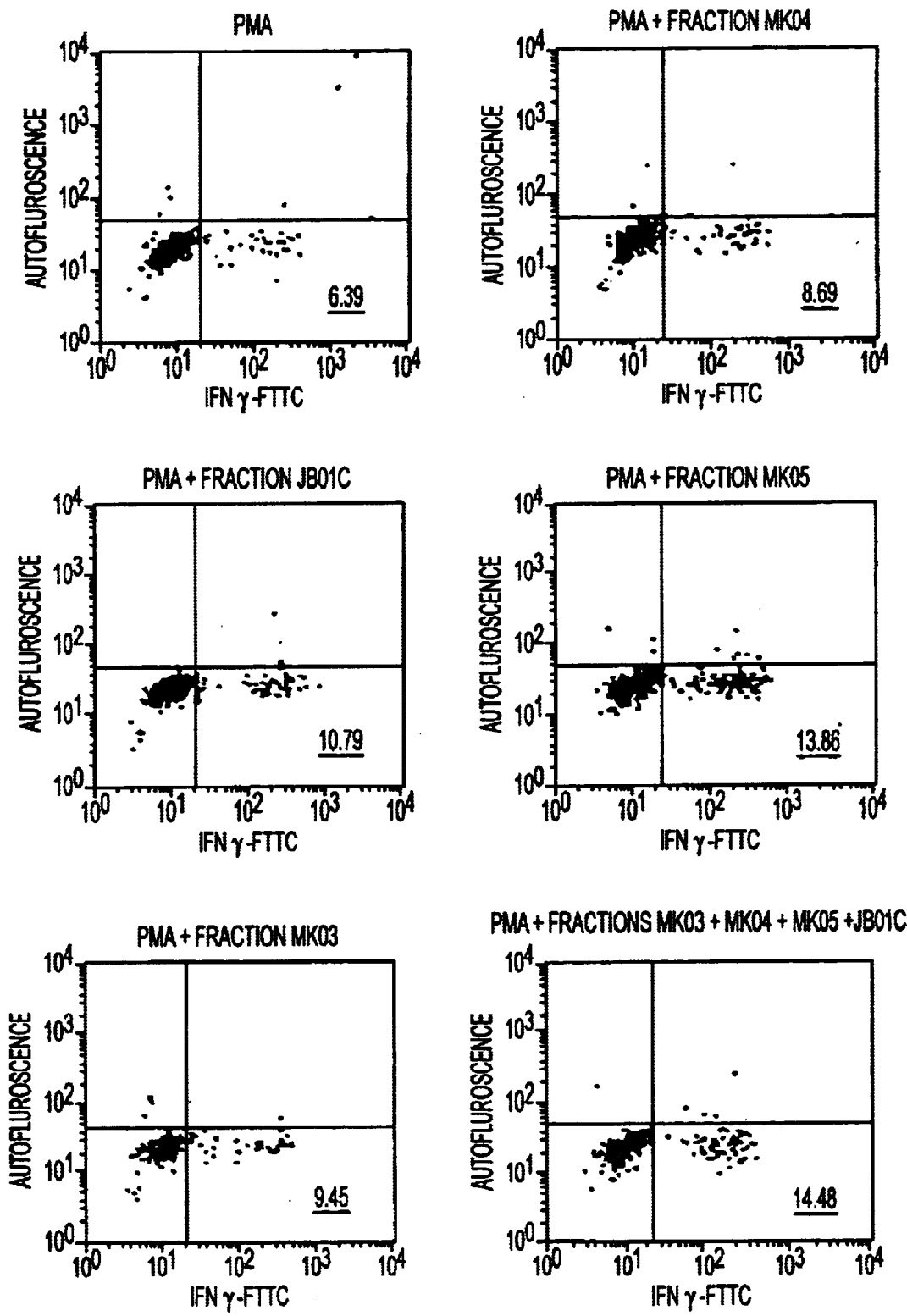
FIG. 1 describes the flow-cytometric determination of intracellular IFN-gamma in ex vivo human mononuclear cells after co-culture with phorbol mysistate acetate (PMA) and calcium ionophore (ionomycin) in the presence or absence of active components obtained from *M. Koenigii* (MK03, MK04, MK05) and *P. betle* (JB01C). Our data indicate that active components MK03, MK04, MK05 and JB01C enhanced IFN-gamma production.
Figure 2:
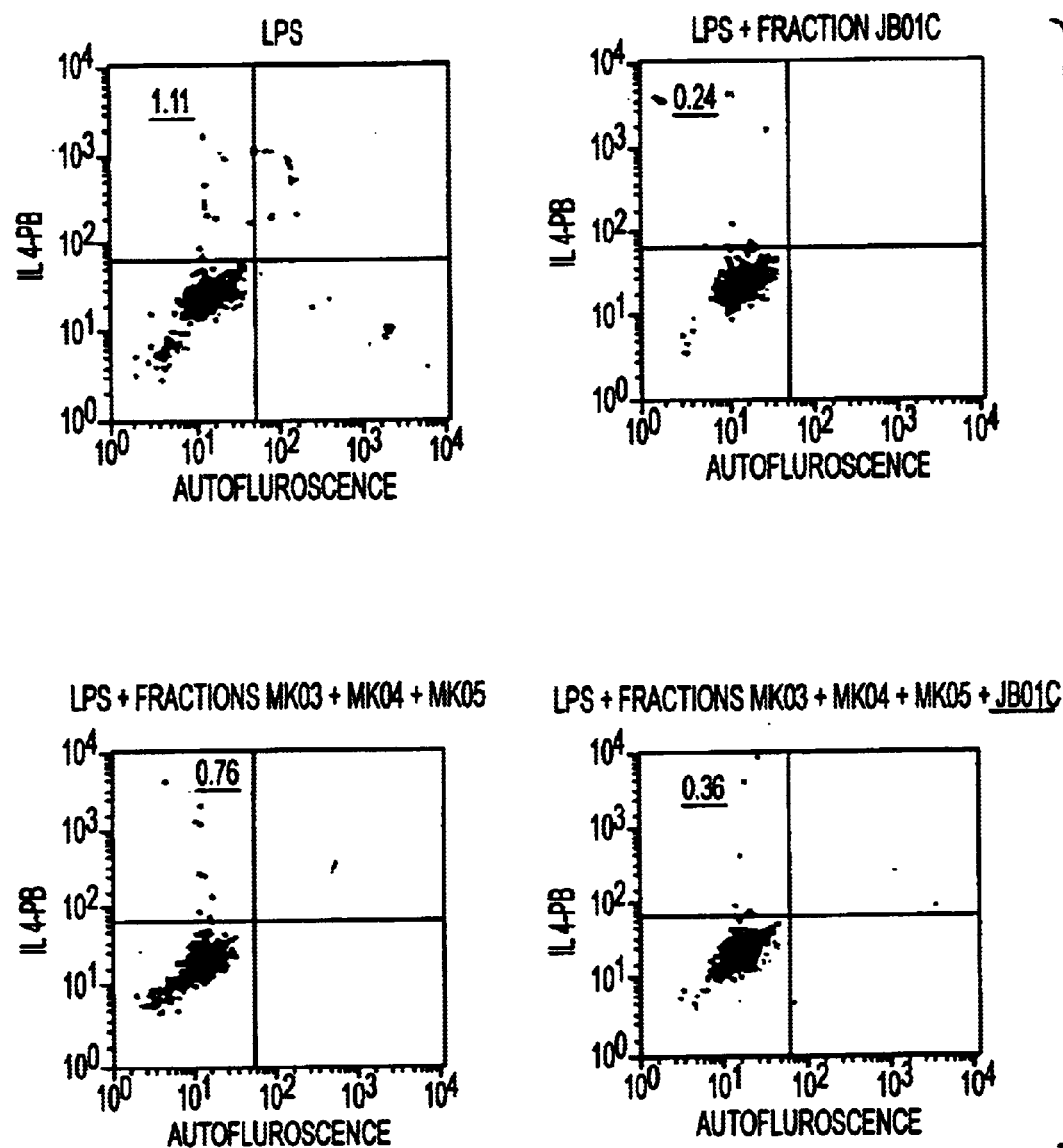
FIG. 2 describes flow-cytometric determination of intracellular IL-4 in ex vivo human neutrophils after coculture with LPS in the presence or absence of components MK03, MK04, MK05 and JB01C. Our data indicate that component JB01C of *P. betle* reduces IL-4 producing cells markedly. On the other hand, components MK03, MK04, MK05 of *Murraya koenigii* had only marginal effects on inhibition of IL-4 production. Of interest, combination of active components MK03, MK04, MK05 of *Murraya koenigii* and active component JB01C of *P. betle* drastically reduces IL-4 production.

Accordingly the present invention provides an pharmaceutical composition useful as leukotriene and IL4 synthesis inhibitor and as Th1 type immunomudulator, said composition comprising effective amount of one or more bioactive components obtained from extracts of plant parts of *Piper betle* (PB) named as JB01A, JB01B and JB01C and bioactive component obtained from the leaf extracts of *Murraya Koenigii* (M.K) named as MK03, MK04 and MK05 optionally associated with or in combination with pharmaceutically acceptable additives.

In an embodiment of the invention, the composition comprises bioactive components selected from the group consisting of MK03, MK04 and MK05.

In an embodiment of the invention, the composition comprises bioactive components selected from the group consisting of JB01C, MK03, MK04 and MK05.

In another embodiment of the invention, the plant parts used is selected from leafs, stems, barks, fruits, seeds or any other plant parts.

In still another embodiment of the invention relates to the additives used for preparing the composition which is selected from nutrients such as proteins, carbohydrates, sugar, talc, magnesium stearate, cellulose, calcium carbonate, starch-gelatin paste and/or pharmaceutically acceptable carriers, excipient, diluent or solvent.

In still another embodiment relates to administration of the composition through oral, intravenous, intramuscular, inhalation, or subcutaneous routes wherein, the oral route is in the form of capsule, syrup, concentrate, powder or granules. The amount of the bioactive component administered by intravenous route is less than the oral route.

In yet another embodiment of the invention wherein, the proportion of M.K active component is equal to or greater than the amount of betle leaf active component and it is in the range between 1:1 to 5:1.

In yet another embodiment of the invention, wherein the composition is administered at a dosage level between 0.5 to 10.0 mg/kg of body weight at least once in a day for a period at least 4 weeks depending upon the respiratory conditions.

In yet another embodiment of the invention herein, the composition is administered at a dosage level between 0.5 to 5.0 mg/kg of body weight at least once in a day for a period at least 4 weeks depending upon the respiratory conditions.

In yet another embodiment of the invention, wherein the composition is administered for a period for at least 4 weeks and up to 3 months, in case of relapse conditions.

In yet another embodiment of the invention, the composition is used for the treatment of bronchial respiratory conditions.

In yet another embodiment of the invention, the composition is used for treating animals or human beings.

In yet another embodiment of the invention, the composition is used for shifting Th2 response to Th1 response.

In yet another embodiment of the invention, the composition is used for inhibiting 5-lipooxygenase mediated Arachidonic acid oxidation in neutrophils enriched component of whole blood.

In yet another embodiment of the invention, the composition is used for enhancing IFN-gamma and reducing IL-4 response in ex-vivo human whole blood.

In yet another embodiment of the invention, the composition is used for enhancing IFN-gamma response in ex vivo human whole blood mononuclear (PMN).

In yet another embodiment of the invention, the composition is used for reducing IL-4 response in human peripheral whole blood mononuclear cells.

One more embodiment of the invention relates to a method of treating a subject for bronchial respiratory conditions, said method comprising administering to the subject effective amount of effective amount of one or more bioactive components obtained from extracts of plant parts of *Piper betle* (PB) named as JB01A, JB01B and JB01C and bioactive components obtained from the leaf extracts of *Murrya Koenigii* (M.K) named as MK03, MK04 and MK05 optionally associated with or in combination with pharmaceutically acceptable additives.

In an embodiment of the present invention, the active components from all plant parts of *M. koenigii* and *P. betle* are mixed with freshly drawn human blood.

In an another embodiment of the present invention, the cells in an ex-vivo human blood system are activated with calcium inophor or the likes.

In an another embodiment of the present invention, the active components are separated from all plant parts including barks, roots, leaves and seeds of *M. koenigii* and *P. betle* by the technique such as solvent fractionation, TLC, HPTLC, HPLC etc.

In an another embodiment of the present invention, the extracts from all plant parts are made from fresh or sunshade dried *M. koenigii* and *P. betle*.

In an another embodiment of the present invention, plant material are used for extraction with appropriate solvent such as methanol or water or buffer in a percolator or the equipment known in the art.

In an another embodiment of the present invention, the extracts of *M. koenigii* and *P. betle* plant parts are concentrated under reduced pressure to save active principle.

In yet another embodiment of the present invention, the concentrates are lyophilized to remove reduced water and other residual solvent.

In yet another embodiment of the present invention, the lyophilized solid is chromatographed using silicagel or Sephadex LH-20 to isolate the pure components.

In yet another embodiment of the present invention, the isolated components of M.K and P.B found active as an inhibitor of 5-lipoxygenase mediated Arachidonic acid oxidation in an ex-vivo whole human blood.

In yet another embodiment of the present invention, the components obtained from the extracts of all plant parts of *M. koenigii* and *P. betle* found active for shifting from Th2 type response to the Th1 response.

In yet another embodiment of the present invention, the active components are selected from the extracts of *M. koenigii* and *P. betle* inhibited 5-lipoxygenase mediated Arachidonic acid oxidation in neutrophils enriched component from whole blood.

In yet another embodiment of the present invention, the active components are selected from the extracts of *M. koenigii* and *P. betle* are found to enhance IFN-gamma response in ex-vivo whole human blood.

In yet another embodiment of the present invention, the active components selected from *M. koenigii* and *P. betle* extracts found to enhance INF-gamma response in ex vivo human blood neutrophils (PMN).

In yet another embodiment of the present invention, the active components selected from the extracts of *M. koenigii* and *P. betle* found to reduce IL-4 response in human peripheral blood mononuclear cells.

In yet another embodiment of the present invention, the components obtained from the extracts of *M. koenigii* and *P. betle* are found as inhibitors of 5-lipoxygenase mediated arachidonic acid oxidation assayed after incubation of whole blood and lysing the cells at the time of assay are chosen for preparing the composition.

In yet another embodiment of the present invention, the lyophilized solid is chromatographed over silica gel or Sephadex LH-20 to isolate the pure active component present in the leaf and all other plant parts of *Murraya koenigii* and *Piper betle* for the use of relief, treatment and cure of respiratory problem.

The following examples are given by way of illustration and therefore should not be construed to limit the scope of the present invention.

EXAMPLE I

Collection of Plant Material

The leaves and all other plant parts of plants of *Murraya koenigii* and *Piper betle* are collected from shrubs and climber respectively from different areas of West Bengal, India. A voucher specimen is deposited at the department of Medicinal Chemistry at the Indian Institute of Chemical Biology, 4 Raja S. C. Mullick Road, Calcutta-700032.

EXAMPLE II

Preparation of the Active Material

Part I (*Murraya koenigii*)

Fresh leaves and all other plant parts including barks, roots and seeds of *Murraya koenigii* collected, cleaned and washed with water after getting from the local supplier and used as starting materials.

410 gm of the fresh leaves and other plant parts of *Murraya koenigii* is made a paste in a mixture-blender in a methanol (1000 ml) and is placed in a glass percolator (5 lit. capacity) with the addition of 1000 ml of methanol. This is kept for 16 hrs (overnight) at room temperature. Filtering the extract through Whatman No.1 filter paper collected the percolate. The process of extraction is repeated four times and the combined extract is evaporated to dryness under reduced pressure in a rotary evaporator, keeping the temperature at 40° C. (bath). The solid residual matter left is viscous in appearance and it is further dried by lyophilization. The yield is 25.63 gm. The schematic diagram of the fractionation procedure is shown in flow diagrams I and II.

Flow Diagram-I

*Murraya koenigii*

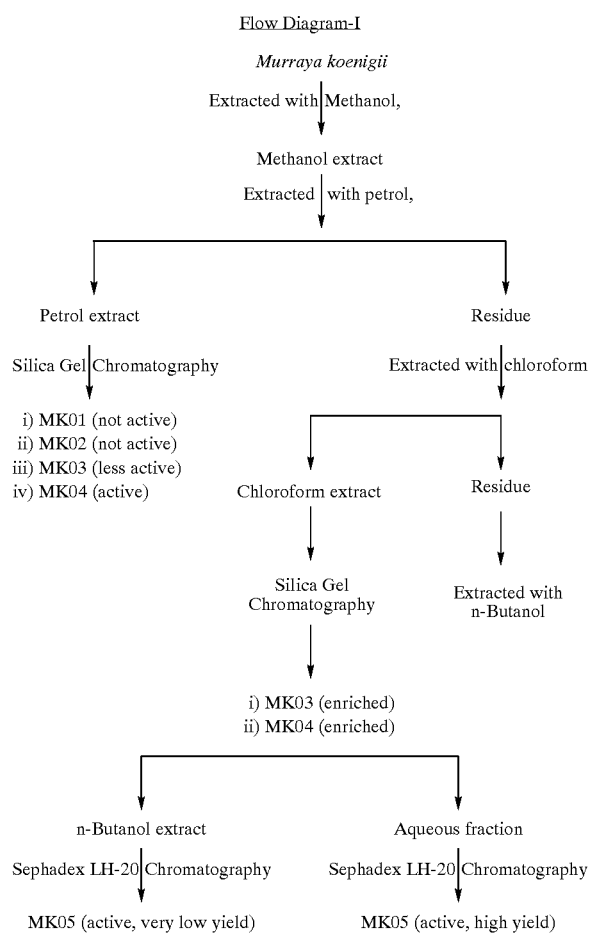

Part II (*P. betle*) Extract

Fresh leaves or all plant parts of *Piper betle* is collected from local supplier and is used as starting material.

200 g of each plant parts is homogenized separately with 300 ml of methanol in a mixture-blender. It is then sonicated in an ultrasonic bath with 3 burst each for 15 min. The extract is filtered through Whatman No. 1 filter paper and the filtrate is collected. This process of extraction is repeated three times. The combined extract is lyophilized yielding a semi-solid man weighing 6.32 g.

A part of this extract (4.00 gm) is chromatographed, over sephadex LH-20 column. Among the isolated components, three designated as JB01A (0.17 g or 70 mg,) JB01B (0.33 g or 330 mg) and JB01C (0.94 g or 940 mg) are found active.

Flow Diagram II

*Piper betle*

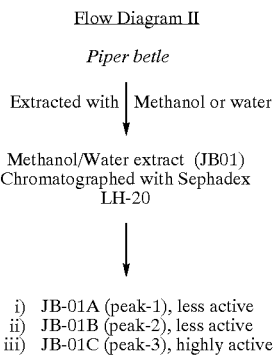

i) JB-01A (peak-1), less active
ii) JB-01B (peak-2), less active
iii) JB-01C (peak-3), highly active

EXAMPLE III

The method of preparation of the active factors comprises:

1. collecting the fresh leaves and all other plant parts from the local suppliers.
2. drying the plant parts under shade to a moderate degree or to take the fresh plant parts as the starting material.
3. powdering the dried or homogenizing each plant parts separately in the apparatus known in the art.
4. putting the powder or homogenate in a percolator under the bulk of appropriate solvents; choosing hydrocarbon solvents such as petroleum ether (B.P.40–60° C.), petroleum ether (B.P.–60° C.–80° C.), pentane, hexane, benzene etc., chlorinated solvents like chloroform, dichloromethane, carbontetrahloride etc., etherial solvents such as diethyl ether, tetrahydrofuran, dioxane etc., ketonic solvents such as acetone, cyclopentanone etc.; ester solvents such as ethyl acetate, ethyl formate etc.; all alcohols such as methanol, ethanol, n-butanol etc., water and buffers.
5. extracting the percolated plant material using a percolator or the apparatus or equipment currently known in the art over a period of time ranging from 1 to 120 hours.
6. Evaporating the solvent under reduced pressure using an apparatus or equipment currently known in the art.
7. Lyophilizing or drying the material in the apparatus or equipment currently known in the art and storing the processed material in a cool and dry place in an air-tight container.
8. Isolation of individual active components by silica gel and Sephadex LH-20 chromatography.
9. Characterization of pure compounds present in the extract to be used as markers for evaluating the bioactivity.
10. Storing the processed material in a cool and dry place in an air tight container.
11. Evaluating the bioactivity of the material.

EXAMPLE IV

Method:

500 $\mu$l of heparinised human peripheral blood half diluted with PBS is taken in each well of a 24-well tissue culture plate. 1 $\mu$g/ml concentration of each sample is added in each well. In case of mixture, the components are mixed at 1:1 ratio to make a final preparation, which is used at a concentration of 1.0 $\mu$g/ml. The cells are then incubated for 3 hr. at 37° C. with occasional shaking. The 10 $\mu$l/ml of arachidonic acid solution (12.2 mg/ml of absolute alcohol stored under argon at –20° C.) is added to each well for 5 min prior to the addition of calcium ionophore (A23187) at a concentration of 20 $\mu$g/ml to continue the incubation for further 10 min. Volume of the cell suspension is made up to 2 ml with PBS and its oxygen content is monitored with the help of a sensitive Oxygraph instrument.

EXAMPLE V

Method:

500 $\mu$l of half diluted human peripheral blood is incubated with 1 $\mu$g/ml of each component for 3 hr. at 37° C. with occasional shaking. In case of mixture, the components are mixed at 1:1 ratio to make a final preparation, which is used at a concentration of 1.0 $\mu$g/ml. Then 10 $\mu$l/ml of arachidonic acid solution (12.2 mg/ml of absolute alcohol stored under argon at –20° C.) is added to each well for 5 min prior to the addition of calcium ionophore (A23187) at a concentration of 20 µg/ml to continue the incubation for further 10 min. Volume of the cell suspension is made up to 2 ml by addition 1 ml of PBS+500 µl of water to lyse the cells. Oxygen content of the cell lysate is monitored in a sensitive Oxygraph instrument.

EXAMPLE VI

Method:

Heparinised human peripheral blood is mixed with equal volume of 2% gelatin solution in PBS and allowed to stand for half an hour when RBC are settled down at the bottom. Upper layer containing neutrophil enriched mononuclear cells is centrifuged and cell pellet is suspended in PBS. 500 µl/ml of this cell suspension ($3\times10^6$ cells/well) is incubated with 1 µg/ml of each component at 37° C. for 3 hrs. In case of mixture, the components are mixed at 1:1 ratio to make a final preparation, which is used at a concentration of 1.0 µg/ml. Then arachidonic acid solution 10 µl/ml (12.2 mg/ml) is added to each well for 5 min prior to the addition of calcium ionophore (A23187) at a concentration of 20 µg/ml to continue the incubation for further 10 min. Volume of the cell is made upto 2 ml with PBS and oxygen content of the cell suspension is monitored in a sensitive Oxygraph instrument.

Thus, active components from the extracts of all plant parts of *M. koenigii* and *P. betle,* have been screened for biological activity relevant to the relief, treatment and cure of asthmatic conditions, and the component thus processed, have been analyzed by Thin Layer chromatography and HPLC and NMR spectra, dissolved and suspended finely in appropriate solvents and used in the test system (ex vivo whole human blood to establish the stipulated biological response).

EXAMPLE VII

A part of *M. koengii* extract (8.01 g) is subjected to silica gel column chromatography that resulted in isolation of components among the biologically active components. These are designated as component MK03 (70 mg), MK04 (270 mg) and MK05 (110 mg).

EXAMPLE VIII

Physicochemical Characterization of MK03, MK04, MK05, JB01A, JB01B and JB01C Component MK03:

1. The dried solid, melting point 98–100° C., soluble in DMSO.
2. Thin layer chromatography shows single spot having Rf 0.48 in one of the solvent systems—chloroform and methanol (19:1).
3. The HPLC analysis shows single peak with retention time 8.5 min. at a flow rate of 0.5 ml/min using intersel ODS-3 (4.6×250 mm) analytical column, solvent system methanol and detection is carried out at 210 nm.

HPLC: Column ODS-3 (4.6×250 mn) Flow rate—0.5 m/min; Peak at 210 nm; Retention time—3.5 min.; Solvent system—methanol.

4. $^{13}$CNMR, ppm (125 MH2, CDCl3): 153.34, 153.29, 148.94, 140.73, 134.78, 131.58, 128.61, 124.22, 120.36, 119.97, 118.23, 118.02, 117.39, 116.63, 108.36, 104.39, 97.16, 78.03, 40.68, 25.67, 25.60, 22.70, 17.53 and 15.97.

5. Component 'MK03' appears to be a pure alkaloid.

Component MK04:

1. Dark colored gummy material soluble in dimethyl sulfoxide.
2. TLC of active material shows single spot having Rf 0.38 in the solvent system of chloroform and methanol (19:1).
3. The HPLC analysis of the active material using intersil ODS-3 analytical column, solvent system methanol and a flow rate 1.0 ml/min, detection at 254 nm shows one peak with retention time 5:69 min.
4. NMR (300 $MH_2$, $CDCl_3$) δ0.94, 1.30, 1.60, 2.04–2.10, 2.27–2.34, 2.78–2.82, 3.53–3.81, 3.85–3.92, 4.00, 4.24–4.26, and 5.26–5.41.
5. The component MK04 is a glycolipid.

Component MK05:

1. Dark colored solid soluble in DMSO and water.
2. TLC shows single spot having Rf 0.66 in the solvent system n-butanol-acetic acid—water (9:5:7).
3. The HPLC analysis of this component shows a peak at retention time 21 min., solvent system methanol—water (1:9), flow rate 0.5 ml/min. and detection at 217 nm.
4. $^{13}$CNMR, ppm (125 MH2, D2O): 175.82, 169.22, 159.00, 147.63, 147.02, 144.76, 135.72, 131.28, 131.10, 129.90, 129.63, 129.20, 128.20, 127.59, 123.30, 116.81, 116.39, 115.80, 114.79, 81.77, 76.26, 76.15, 74.20, 73.79, 73.64, 73.49, 72.84, 72.16, 71.34, 70.29, 69.89, 68.83, 67.96, 63.71, 63.14, 58.22, 56.62, 56.19, 54.47, 54.42, 54.37, 41.90, 36.87 and 20.93.
5. The component MK05 appears to be aromatic compound conjugated with sugars.

Component JB01A

1. White color solid material and soluble in both DMSO and water.
2. TLC shows single spot having Rf 0.07 in the solvent system n-Butanol-acetic acid—water (9:5:7).
3. HPLC shows a peak at retention time 8.4 min. (JB01A, peak-1) with solvent system water-methanol (9:1), flow rate 0.5 ml/min, detection at 217 nm and intersil ODS-3 analytical column.
4. $^{13}$CNMR, ppm (125 MH2, D2O): 109.71, 108.417, 107.94, 104.17, 100.27, 84.38, 81.79, 81.53, 80.74, 77.03, 75.58, 73.85, 73.42, 71.71, 71.27, 70.74, 70.38, 69.12, 61.71, 61.00 and 60.54.
5. Component JB01A is oligosaccharide.

Component JB01B:

1. White color solid soluble in both DMSO and water.
2. TLC shows single spot having Rf 0.27 in the solvent system n-butanol-acetic acid—water (9:5:7).
3. HPLC shows a peak, at retention time at 8.8 min (JB01B, peak-2) with the same above column condition.
4. $^{13}$CNMR, ppm (125 MH2, D2O): 169.48, 104.30, 98.86, 98.55, 92.60, 81.82, 76.98, 76.07, 74.57, 73.52, 73.23, 71.78, 71.46, 70.02, 69.84, 69.74, 69.30, 68.92, 68.77, 67.01, 66.43, 62.95, 62.02, 61.61, 48.67, 44.62, 38.88.
5. Component is JB01B an oligosaccharide derivative.

Component JB01C:

1. White solid soluble in both DMSO and water.
2. TLC shows single spot having Rf 0.34 in solvent system n-butanol—acetic acid—water (9:5:7).
3. HPLC shows single peak at retention time 9.8 min. (JB01C, peak-3) with the same above condition.
4. NMR (300 $MH_2$, $D_2O$). 2.34. 3.27, 3.28, 3.44–3.47, 3.51, 3.60–3.63, 3.68, 3.92–3.99, 4.08, 4.92 and 5.36.
5. Component JB01C is a oligosaccharide.

EXAMPLE IX

Description of Test for Analyzing Intracellular Interferon Gamma (IFN-γ) and Interleukin-4 (IL-4) by flowcytometry Method: Heparinized whole blood (0.1 ml/well of 24 well plates, collected from normal individuals) are cultured at 37° C. in 5% $CO_2$ for 6 hours in a total volume of 1.0 ml Rosewell Park Memorial Institute (RPMI) medium containing 10% heat inactivated fetal bovine serum and phorbol myristate acetate (PMA) and inomycin or LPS in the presence or absence of fractions from all plant parts of *P. betle* and *M. koenigii* (50.0 μg/ml each) either alone or in combination. To cause the intracellular accumulation of newly synthesized proteins, brefeldin A (10 μg/ml) is added to the cells for last 4 hours. At the end of incubation period, cells are treated with FACS™ lysing solution (Becton Dickinson, USA) for lysis of RBC. Cells are then washed, permeabilized by treatment with 4% paraformaldehyde for 10 minutes. After washing with washing buffer (phosphate buffered saline [PBS] containing 1% albumin, 0.1% saponin and 0.1% sodium azide), permeabilized cells are treated with either FITC-labeled anti-IFN-γ monoclonal antibody or PE-labeled anti-IL-4 monoclonal antibody for 20 minutes in room temperature at dark. Cells are washed with washing buffer and then re-suspended in PBS containing 1% paraformaldehyde for single color flow cytometric analysis using FACS Calibur (Becton Dickinson, USA) with the programme Cell Quest. Ten thousand cells are collected for each sample and the fluorescence intensity is measured on a logarithmic scale. To make sure that only intracellular IFNγ or IL-4 is being detected, cells are stained with FITC-labeled anti-IFNγ or PE-labeled anti-IL-4 antibody before permealization and gave less than 0.2% fluorescent cells for each staining. Irrelevant isotype-matched control antibody also produced only less than 0.1% fluorescent cells.

TABLE 1 showing results of examples IV to V

| Bioactive Components | % inhibition of $O_2$ consumption | | |
|---|---|---|---|
| | Example IV | Example V | Example VI |
| None | — | — | — |
| MK03 | 12.75 | 10.16 | 11.68 |
| MK04 | 86.42 | 76.57 | 87.40 |
| MK05 | 80.45 | 79.70 | 89.84 |
| JB01C | 3 | 5.42 | 4.58 |
| MK03 + MK04 + MK05 | 81 | 89.62 | 88.76 |
| MK03 + MK04 + MK05 + JB01C | 77.73 | 83.20 | 85.94 |

What is claimed is:

1. A pharmaceutical composition useful as a leukotriene and IL4 synthesis inhibitor and as a Th1 type immunomudulator, said composition comprising a pharmaceutically effective amount of (A) one or more bioactive components JB01A, JB01B and JB01C, which are obtained from the plant *Piper Betle* and (B) one or more bioactive components MK03, MK04 and MK05, which are obtained from the plant *Murraya Koenigii;* wherein said bioactive components are optionally associated with or in combination with a pharmaceutically acceptable additive.

2. The composition as claimed in claim 1, wherein the additive is selected from nutrients, proteins, carbohydrates, sugar, talc, magnesium stearate, cellulose, calcium carbonate, starch-gelatin paste a pharmaceutically acceptable carrier, excipient, diluent or solvent.

3. The composition as claimed in claim 1, wherein the composition is suitable for administration by oral, intravenous, intramuscular, inhalation, or subcutaneous routes.

4. The composition as claimed in claim 1, wherein the composition is in the form of a capsule, syrup, concentrate, powder or granules.

5. The composition as claimed in claim 3, wherein the amount of bioactive component in the composition for administration by the intravenous route is less than the amount of bioactive component in the composition for administration by the oral route.

6. The composition as claimed in claim 1, wherein the amount of *Murraya Koenigii* active components is equal to or greater than the amount of *Piper Betle* active component.

7. The composition as claimed in claim 1, wherein the ratio of bioactive component obtained from *Piper Betle* to the bioactive component obtained from *Murraya Koenigii* is in the range between 1:1 to 1:5.

8. A method of treating a respiratory condition in a patient in need thereof comprising administering the composition as claimed in claim 1, wherein the composition is administered at a dosage level between 0.5 to 10.0 mg/kg of body weight at least once in a day for a period at least 4 weeks depending upon the respiratory conditions.

9. The method as claimed in claim 8, wherein the composition is administered for a period of 4 weeks to 3 months.

10. The method as claimed in claim 8, wherein the composition is administered again in case of relapse conditions.

11. The method as claimed in claim 8, wherein the respiratory condition is a bronchial respiratory condition.

12. The method as claimed in claim 8, wherein the patient is a human being.

13. The method as claimed in claim 8, wherein the composition shifts the Th2 response to the Th1 response.

14. A method of inhibiting 5-lipooxygenase mediated Arachidonic acid oxidation in neutrophils enriched component of whole blood, comprising administering the composition of claim 1 to a patient in need thereof.

15. A method of enhancing IFN-gamma and reducing IL-4 response in ex-vivo human whole blood, comprising administering the composition of claim 1 to a patient in need thereof.

16. A method of enhancing IFN-gamma response in ex vivo human whole blood mononuclear (PMN).

17. A method of reducing IL-4 response in human peripheral whole blood mononuclear cells.

18. The method of as claimed in claim 8, wherein the patient is an animal.

* * * * *